April 20, 1971 C. M. AKEHURST Plant Pat. 3,048
AZALEA PLANT
Filed April 1, 1969
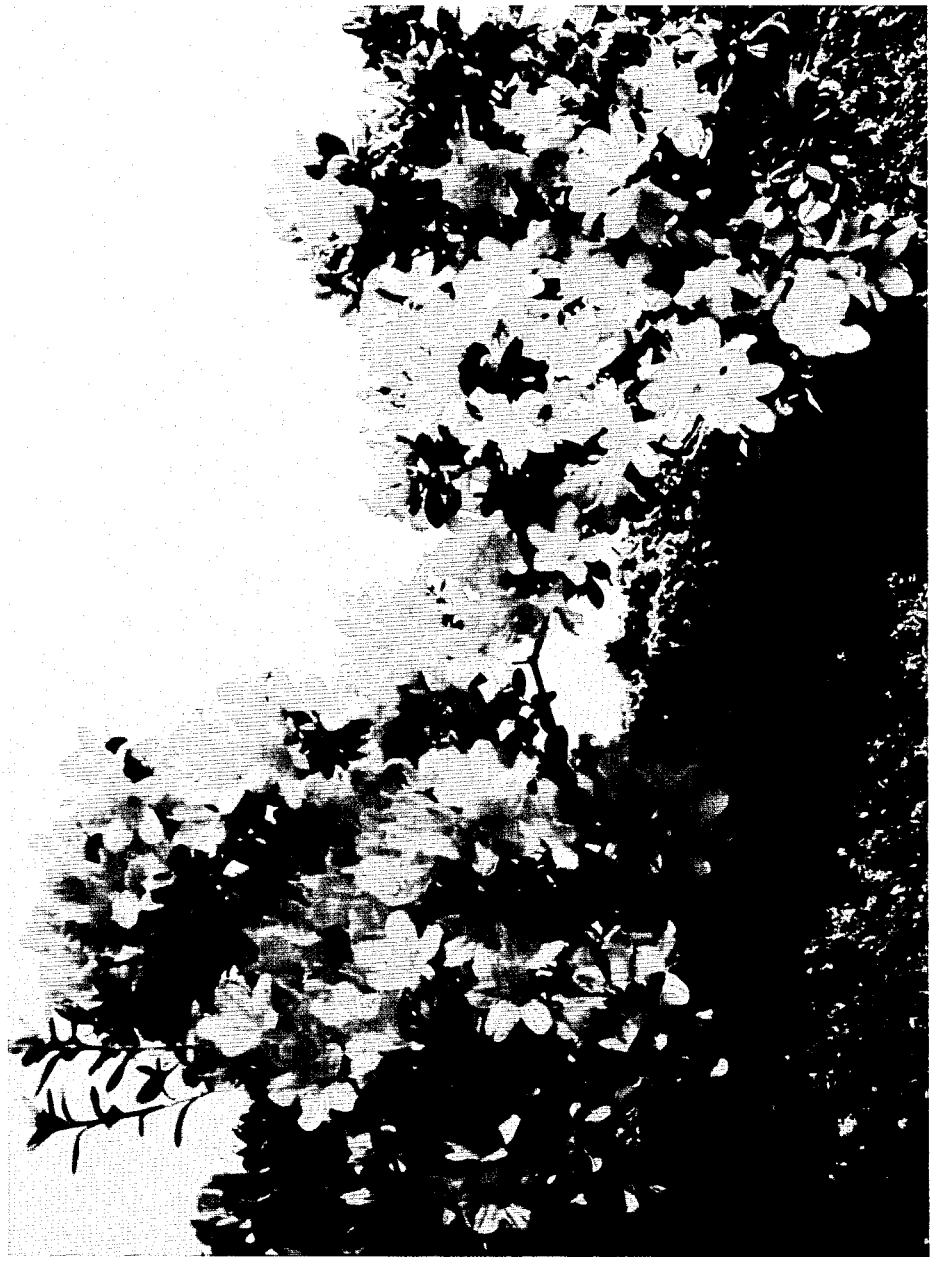
Inventor
Carville M. Akehurst
By
Burns, Doane, Swecker & Mathis
Attorneys United States Patent Office Plant Pat. 3,048
Patented Apr. 20, 1971

3,048
AZALEA PLANT

Carville M. Akehurst, Perry Hall, Md., assignor to
Akehurst Nurseries, Perry Hall, Md.

Filed Apr. 1, 1969, Ser. No. 812,474
Int. Cl. A01h 5/00
U.S. Cl. Plt.—57 1 Claim

ABSTRACT OF THE DISCLOSURE

An azalea plant which is a sport of the azalea Hino Crimson, but with Empire Rose flowers.

The present invention relates to a new and distinct variety of azalea plant which was discovered as a sport of the azalea variety known as Hino Crimson (unpatented).

At the time of my discovery, the original plant thereof was growing in a cold frame among several thousand Hino Crimson plants in the same size pots, all of which were in a cultivated state and all of which were of the same crop and were being grown under my direction and control in a cold frame at Akehurst Nurseries, Perry Hall, Md.

The accompanying drawing shows a typical specimen of my new azalea plant (on the left in the illustration) as compared with Hino Crimson (on the right) as depicted in color as nearly true as is reasonably possible to make same in a color illustration of this character.

In the following description reference is made to the British Horticultural Color Chart.

The distinctive quality of the plant is its flower, which is Empire Rose (062/1). Some blossoms have a red blotch (delft rose, 020/1). As such, the flowers are distinctive in color from Hino Crimson. The bud of the new plant before opening appears to be red (cardinal red, 822) and can be distinguished readily from Hino Crimson in the same state.

The size of the plant and the size of the flower are the same as the parent Hino Crimson and is similar in appearance as far as the foliage is concerned. The plant has a compact form of growth; the leaves are persistent, small and glossy, and the open flower measures one and one-quarter inches across. The new variety comes into flower at the same time as does Hino Crimson. It is also fully as winter hardy.

The plant has been propagated asexually by cuttings at Akehurst Nurseries, Perry Hall, Md., which were first rooted in the fall of 1955 and in subsequent years. These plants were grown into larger sizes and tested for growth and winter hardiness.

I claim:

1. A new and distinct variety of azalea plant substantially as herein shown and described, characterized particularly as to novelty by its Empire Rose flower with some of the flowers having a red blotch and with a red bud before opening, all distinct from its parent, Hino Crimson, while the size and appearance of the plant including its foliage and shape is substantially the same as the parent, Hino Crimson.

No references cited.

ROBERT E. BAGWILL, Primary Examiner